(12) United States Patent
Theno

(10) Patent No.: US 10,667,491 B2
(45) Date of Patent: Jun. 2, 2020

(54) PET DEVICE

(71) Applicant: Bioesse Technologies, LLC, Minnetonka, MN (US)

(72) Inventor: Mark H Theno, Minnetonka, MN (US)

(73) Assignee: Bioesse Technologies, LLC, Minnetonka, MN (US)

( * ) Notice: Subject to any disclaimer, the term of this patent is extended or adjusted under 35 U.S.C. 154(b) by 176 days.

(21) Appl. No.: 15/616,488

(22) Filed: Jun. 7, 2017

(65) Prior Publication Data
US 2018/0352784 A1 Dec. 13, 2018

(51) Int. Cl.
*A01K 13/00* (2006.01)
*A61M 21/02* (2006.01)
*A61D 7/00* (2006.01)
*A61M 21/00* (2006.01)

(52) U.S. Cl.
CPC .............. *A01K 13/003* (2013.01); *A61D 7/00* (2013.01); *A61M 21/02* (2013.01); *A61M 2021/0016* (2013.01); *A61M 2209/088* (2013.01); *A61M 2250/00* (2013.01)

(58) Field of Classification Search
CPC .... A01K 13/003; A61D 7/00; A61M 2258/00
See application file for complete search history.

(56) References Cited

U.S. PATENT DOCUMENTS

| | | | | | |
|---|---|---|---|---|---|
| 1,732,028 | A | * | 10/1929 | Reiner | A01M 1/2044 119/654 |
| 2,808,030 | A | * | 10/1957 | Costanzo | A01K 27/007 119/860 |
| 3,477,409 | A | * | 11/1969 | Costanzo | A01K 27/007 119/174 |
| 3,687,114 | A | * | 8/1972 | Berkstresser | A01K 27/007 119/654 |
| 3,949,708 | A | * | 4/1976 | Meeks | A01K 11/001 119/655 |
| 4,355,599 | A | * | 10/1982 | Fickes | A01K 13/003 119/654 |
| 4,574,742 | A | * | 3/1986 | Morgan, Jr. | A01K 13/003 119/654 |
| 4,694,781 | A | * | 9/1987 | Howe | A01K 13/003 119/655 |
| 4,926,784 | A | * | 5/1990 | Brightful | A01K 13/00 119/653 |
| 5,049,143 | A | * | 9/1991 | Gertner | A61D 7/00 604/304 |
| D444,599 | S | * | 7/2001 | Guerry, Jr. | D20/27 |
| 2011/0192911 | A1 | * | 8/2011 | Bevins | A01K 13/003 239/36 |
| 2012/0196056 | A1 | * | 8/2012 | Fox | A01K 13/003 428/34.1 |

FOREIGN PATENT DOCUMENTS

FR 2126487 A5 * 10/1972 ........... A01K 13/003
WO WO-2018073628 A1 * 4/2018 ............... A61D 7/00

* cited by examiner

*Primary Examiner* — Kristen C Hayes
(74) *Attorney, Agent, or Firm* — Schwegman Lundberg & Woessner, P.A.

(57) ABSTRACT

Disclosed is a pet device. The pet device may include a housing and a porous element. The housing may define a cavity and including a front portion. The front portion may define a plurality of through holes passing from an exterior surface of the housing to the cavity. The porous element may be size to fit within the cavity. The porous element may be impregnate with a first substance.

20 Claims, 3 Drawing Sheets

PET DEVICE

TECHNICAL FIELD

Embodiments described generally herein relate to pet devices. Some embodiments relate to a device for dispensing a vapor proximate a pet.

BACKGROUND

Millions of Americans own animals as pets. To many, their pets are treated as members of the family. To that end, Americans spend billions of dollars a year on items for their pets. These items may include, special foods, toys, clothing, and furniture (e.g., monogramed dog beds).

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
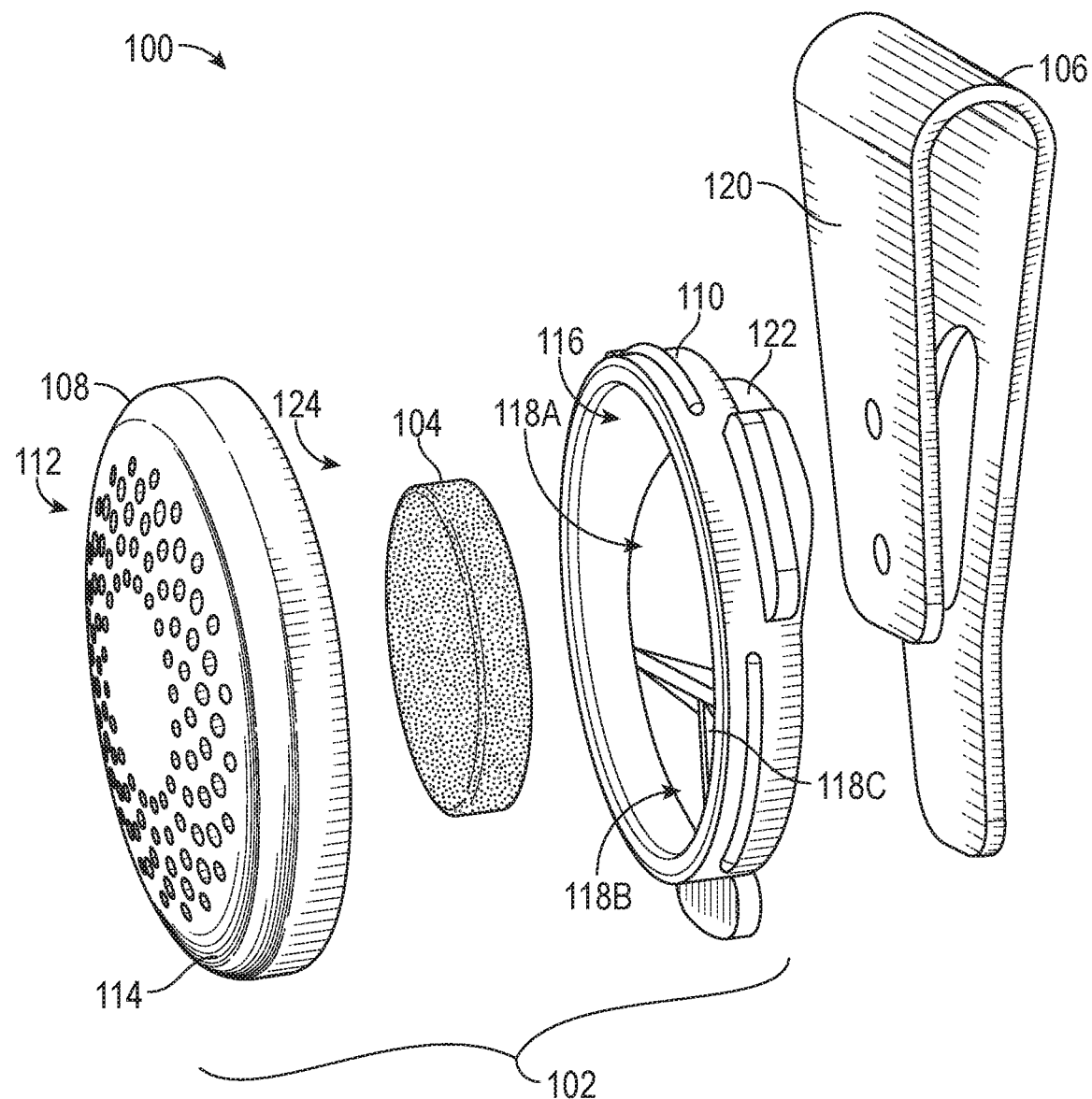
FIG. 1 illustrates an exploded assembly of a pet device in accordance with embodiments disclosed herein.

Animals can experience anxiety, stress and depression. The anxiety, stress and depression can cause the animals to display physical symptoms of distress or behavior that may be destructive. For example, when an animal, such as a pet, is separated from its owner or another animal (e.g., a second pet, its mom, etc.) the animal may experience anxiety or depression. The anxiety or depression may cause the animal to display physical symptoms such as, but not limited to, loss of appetite and lethargic behavior. The anxiety or depression may also cause the animal to destroy furniture or other items around a house. Stress can be induced to the animal through putting them into a carrier (they may think it is a trip to the Vet), or just transporting them be it a dog, cat or horse, can induce stress.

As disclosed herein, various scents can be used to relieve anxiety and depression in pets. The scents can be delivered via devices attached to collars, bridals, or other articles attached to the pet. For example, the devices disclosed herein can attach to a collar of a dog or cat or a bridal of a horse.

The device may include a housing that defines a cavity. A porous element may be impregnated with one or more substances. The housing may also define a plurality of through holes that pass from an exterior surface of the housing to the cavity. The one or more substances may evaporate or otherwise emit an aroma. The aroma of the one or more substances may help to alleviate anxiety in the animal. For example, the porous element may be impregnated with a plant oil and sweat or other bodily fluids of a sibling or parent of the animal. The plant oil and other fluid may slowly evaporate from the porous element and be inhaled by the animal. Other substances that may be impregnated within the porous element include, but are not limited to, phystosterols (plant sterols), fatty acids, terpene hydrocarbons, monoterpene hydrocarbons, sesquiterpenes, carboxylic acids and their derivatives, sebum, triglycerides, and sapienic acid. In addition, the porous element may be impregnated with oxygenated compounds such as, but not limited to, phenols, alcohols, aldehydes, ketones, esters, lactones, coumarins, ethers, and oxides. Examples of alcohols include, but are not limited to, monoterpene alcohols, sesquiterpene alcohols, diols, and thiols.

In addition to oils or bodily fluids, medications also may be impregnated within the porous element. For example, the animal may have a sensitivity to airborne substances (e.g., pollen) and the medication impregnated within the porous element may be an antihistamine. Other examples of medications may include asthma medication.

The porous element may be changeable. For instance, the housing may allow access to the cavity so that the user can change the porous element when all of the impregnated material has been used up. In addition, the user may be able to change the porous element so that a different aroma is emitted. For instance, the porous element may be impregnated with a perfume. The owner may be able to change the perfume to suit his or her desires.

Turning now to the figures, FIG. 1 illustrates an exploded assembly of a pet device 100 in accordance with embodiments disclosed herein. As shown in FIG. 1, the pet device 100 may include a housing 102, a porous element 104, and a clip 106. The housing 102 may include a first portion 108 and a second portion 110. The first portion 108 may define a plurality of through holes 112 that pass from a first surface 114 of the first portion 108 to a cavity 116 defined by the housing 102.

The cavity 116 may be sized to house the porous element 104. In addition, the cavity 116 may be sized to house porous elements of differing sizes. For example, the porous element 104 may be sized to administer a specific dosage over a specific time. For instance, a porous element of a first size may deliver a dosage of W mg over X hours. A porous element of a second size may deliver a dosage of Y mg over Z hours.

In addition, the cavity 116 may be divided into multiple sections 118A, 118B, and 1180 (collectively, sections 118). The sections 118 may allow the user to put multiple porous elements inside the cavity 116. In addition, the sections 118 may allow the user to store additional porous elements in the cavity 116. For example, a first porous element may be located in section 118A and a second porous element may be located in section 118B. The second porous element may be in a sealed wrapper to inhibit the substance impregnated within the second porous element from evaporating until the user unwraps it.

The housing 102 may be manufactured from a metal, polymer, ceramic, or any combination thereof. For example, the first portion 108 may be manufactured from a polymer via injection molding. The second portion 110 may be made of a metal or ceramic via machining on a CNC machine.

The clip 106 may be separable from the housing 102. As shown in FIG. 1, the clip 106 may include a tab 120. The tab 120 may be inserted into an opening 122 defined by the second portion 110. The clip 106 may allow the pet device 100 to be clipped to a collar or bridal of an animal. The clip 106 may be manufactured from a metal or polymer and may be manufactured via stamping, injection molding, etc.

The clip 106 may also include a barb or other element that may interact with a collar or bridal to prevent the pet device 100 from becoming detached. For example, when a dog scratches, it may inadvertently strike the pet device 100. The barb may protrude from the clip 106 or the housing 102 and act as a barrier to help prevent the pet device 100 from sliding off of the dog's collar.

The porous element 104 may be made of a ceramic or polymer. The porous element may define a plurality of pores 124. The pores 124 may have a diameter that ranges from about 60 to about 90 microns. The size of the pores 124 may control the rate of evaporation. For example, a pore of size X may allow for faster evaporation than a pore of size Y, where X is greater than Y. Stated another way, the pore size may affect evaporation rate by affecting the diffusion of the material in the pores into the atmosphere. For example, assuming a cylindrical pore and using Fick's Law, the time for the substance to evaporate from a pore may be:

$$t = \frac{\rho_w L^2}{2D\rho_s(1-f)}$$

where t=time, $\rho_w$=the density of the substance, L is the length of the pore, D=the diameter of the pore, $\rho_s$=the saturation density of the substance, and f=relative humidity.

As disclosed herein, the substance impregnated within the porous element 104 can be a medication, an oil such as an essential oil or plant oil, a body fluid, such a sweat from a parent or sibling, etc.

Figure 2:
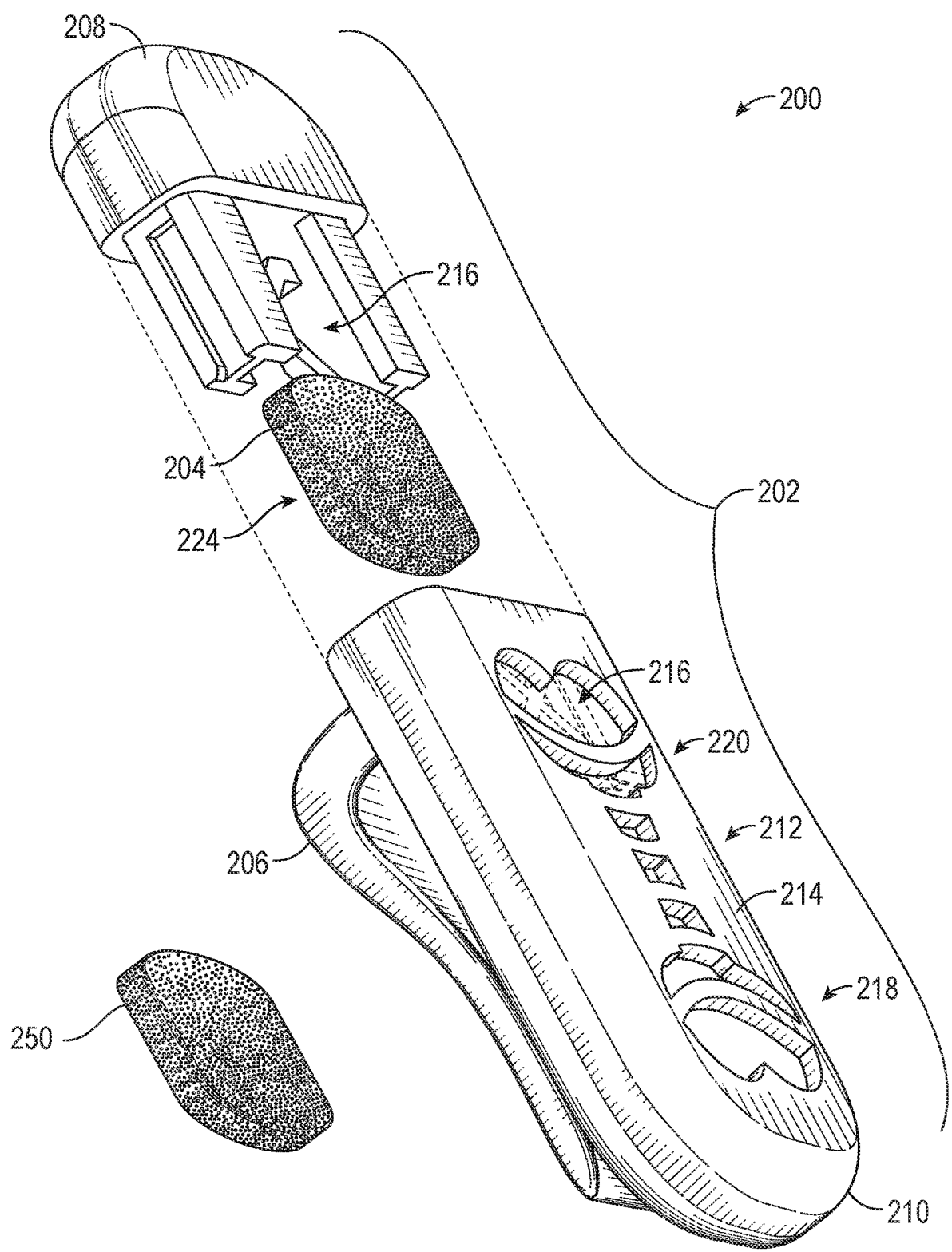
FIG. 2 illustrates an exploded assembly of a pet device in accordance with embodiments disclosed herein.

FIG. 2 illustrates an exploded assembly of a pet device 200 in accordance with embodiments disclosed herein. As shown in FIG. 2, the pet device 200 may include a housing 202 and a porous element 204. The housing 202 may include a first portion 208 and a second portion 210. The second portion 210 may define a clip 206 and a plurality of through holes 212. The plurality of through holes 212 may pass from a first surface 214 of the first portion 210 to a cavity 216 defined by the housing 202. In addition, the plurality of through holes 212 may form an ornamental shape. For instance, as shown in FIG. 2, the plurality of through holes 212 may form an outline of a dog bone. Other non-limiting examples of an ornamental shape may include, a paw, a heart, a hoof etc.

The cavity 216 may be sized to house the porous element 204. In addition, the cavity 216 may be sized to house porous elements of differing sizes. For example, the porous element 204 may be sized to administer a specific dosage over a specific time. For instance, a porous element of a first size may deliver a dosage of W mg over X hours. A porous element of a second size may deliver a dosage of Y mg over Z hours.

In addition, the cavity 216 may be sized to house more than one porous element 204. For example, the cavity 216 may allow the user to store additional porous elements in the cavity 216. For instance, a first porous element may be located at a first end 218 of the second portion 210 and a second porous element may be located at a second end 220 of the second portion 210. The second porous element may be in a sealed wrapper to inhibit the substance impregnated within the second porous element from evaporating until the user unwraps it.

The housing 202 may be manufactured from a metal, polymer, ceramic, or any combination thereof. For example, the first portion 208 may be manufactured from a polymer via injection molding. The second portion 210 may be made of a metal or ceramic via machining on a CNC machine.

While FIG. 2 shows the clip 206 being a continuous extension of the second portion 210, the clip 206 may be separable from the second portion 206. For example, the clip 206 may include a tab that can be inserted into a hole or pocket formed in the second portion as described above with respect to FIG. 1. The clip 206 may allow the pet device 200 to be clipped to a collar or bridal of an animal.

The porous element 204 may be similar to porous element 104 described above. As such, the porous element 204 may be impregnated with a substance that can be a medication, an oil such as an essential oil or plant oil, a body fluid, such a sweat from a parent or sibling, etc. The pores 224 of the porous element 204 may be used to control evaporation of the substance impregnated within the porous element 204 as described above.

The pet devices 100 and 200 disclosed herein may be part of a system. The system may include a plurality of porous elements. The plurality of porous elements may be part of a blister pack of porous elements. Each of the porous elements in the blister pack may be the same or may be different. For example, each of the porous elements may include the same oil that may relieve anxiety within an animal. Alternatively, each of the porous elements may include a different oil or other substances in the same or different dosages.

During manufacturing, the porous elements may be place in a front portion of the blister pack. The substance to be impregnated within the porous elements may be diluted with a substance (e.g., an alcohol). The diluted substance may be allowed to soak into or otherwise impregnate the porous elements. Once the substance has been impregnated with the substance, the dilution agent (e.g., the alcohol) can be flashed off. Stated another way, once the substance has been impregnated into the porous elements, the dilution agent can be heated above its vaporization temperature and boiled off. Thus, the dilution agent should be selected such that it has a vaporization temperature that is significantly below the vaporization temperature of the substance to be impregnated into the porous elements. In addition, the dilution agent should not form an azeotrope with the substance.

The system may also include one or more applicators 250. The applicators 250 may be used to collect a second substance that is to be impregnated into the porous element. For example, the applicators 250 may be alcohol swabs. A pet owner may use the alcohol swabs to collect a sample of a body fluid such as sweet or other oils that can be collected from the skin. The alcohol may act as a dilution agent. Thus, once the body fluid has been absorbed by the porous element, the alcohol may evaporate as described above leaving the body fluid in the pores of the porous element.

Figure 3:
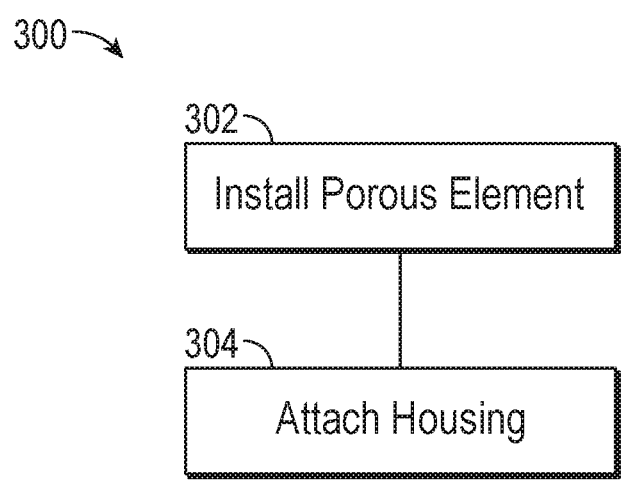
FIG. 3 illustrates a method in accordance with embodiments disclosed herein.

FIG. 3 illustrates a method 300 for providing aroma therapy to a pet in accordance with embodiments disclosed herein. The method 300 may begin at stage 302 where a porous element may be installed in a housing. For example, as disclosed above, the porous element 104 may be installed in the housing 102.

At stage 302 the owner may impregnate additional substances within the porous element. For example, the owner may use an alcohol swab to collect a sample of a parent or sibling's body fluid, such as sweat. During the process, the alcohol may dilute the body fluid such that the body fluid penetrates the pores of the porous element. Once the body fluid has impregnated the porous element, the alcohol may evaporate more quickly than the body fluid leaving the body fluid and the first substance within the porous element.

From stage 302, the method 304 may proceed to stage 304 where the housing may be attached to a pet. Once attached to the pet, the substance impregnated within the porous element may evaporate and be inhaled by the pet.

EXAMPLES

Example 1 includes a pet device. The pet device includes a housing and a porous element. The housing may define a cavity and may include a front portion. The front portion may define a plurality of through holes passing from an exterior surface of the housing to the cavity. The porous element may be sized to fit within the cavity. The porous element may be impregnated with a first substance.

In Example 2, the pet device of Example 1 may optionally include the first substance being an oil.

In Example 3, the pet device of Example 1 may optionally include the first substance being a medication.

In Example 4, the pet device of Example 1 may optionally include a clip for attaching the pet device to a pet.

In Example 5, the pet device of Example 1 may optionally include the porous element being impregnated with a second substance.

In Example 6, the pet device of Example 1 may optionally include the plurality of through holes defining an ornamental shape.

In Example 7, the pet device of Example 6 may optionally include the ornamental shape resembling a dog bone.

In Example 8, the pet device of Example 1 may optionally include the housing including a first portion and a second portion. The first portion separable from the second portion. The exterior surface being a component of the first portion.

Example 9 may include a system for providing aroma therapy to a pet. The system may include a housing, a plurality of porous elements, and applicator. The housing may define a cavity. The housing may include a first surface that defines a plurality of through holes passing from the first surface to the cavity. The plurality of porous elements may be impregnated with a first fluid. Each of the porous elements may be sized to fit within the cavity. The applicator may be for depositing a second fluid onto a surface at least one of the plurality of porous elements.

In Example 10, the system of Example 9 may optionally include the first fluid including an oil.

In Example 11, the system of Example 9 may optionally include the first fluid including a medication.

In Example 12, the system of Example 9 may optionally include the second fluid including an alcohol.

In Example 13, the system of Example 9 may optionally include a clip for attaching the housing to a pet.

In Example 14, the system of Example 9 may optionally include the plurality of through holes defining an ornamental shape.

In Example 15, the system of Example 14 may optionally include the ornamental shape resembling a dog bone.

In Example 16, the system of Example 9 may optionally include the plurality of porous elements being housed in a blister pack.

In Example 17, the system of Example 9 may optionally include the housing including a first portion and a second portion. The first portion separable from the second portion. The exterior surface being a component of the first portion.

Example 18, may include a method for providing aroma therapy to a pet. The method may include installing a porous element in a housing, the housing defining a plurality of through holes and a cavity, the plurality of through holes extend from an exterior surface of the housing to the cavity, the porous disk including a first substance; and attaching the housing to a pet, wherein while attached to the pet, the first substance evaporates from the porous element and is inhaled by the pet.

In Example 19, the method of Example 18 may optionally include the first substance being a medication.

In Example 20, the method of Example 18 may optionally include impregnating the porous element with a second substance prior to installing the porous element in the housing.

The above detailed description includes references to the accompanying drawings, which form a part of the detailed description. The drawings show, by way of illustration, specific embodiments that may be practiced. These embodiments are also referred to herein as "examples." Such examples may include elements in addition to those shown or described. However, also contemplated are examples that include the elements shown or described. Moreover, also contemplate are examples using any combination or permutation of those elements shown or described (or one or more aspects thereof), either with respect to a particular example (or one or more aspects thereof), or with respect to other examples (or one or more aspects thereof) shown or described herein.

Publications, patents, and patent documents referred to in this document are incorporated by reference herein in their entirety, as though individually incorporated by reference. In the event of inconsistent usages between this document and those documents so incorporated by reference, the usage in the incorporated reference(s) are supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to suggest a numerical order for their objects.

The above description is intended to be illustrative, and not restrictive. For example, the above-described examples (or one or more aspects thereof) may be used in combination with others. Other embodiments may be used, such as by one of ordinary skill in the art upon reviewing the above description. The Abstract is to allow the reader to quickly ascertain the nature of the technical disclosure and is submitted with the understanding that it will not be used to interpret or limit the scope or meaning of the claims. Also, in the above Detailed Description, various features may be grouped together to streamline the disclosure. However, the claims may not set forth features disclosed herein because embodiments may include a subset of said features. Further, embodiments may include fewer features than those disclosed in a particular example. Thus, the following claims are hereby incorporated into the Detailed Description, with a claim standing on its own as a separate embodiment. The scope of the embodiments disclosed herein is to be determined with reference to the appended claims, along with the full scope of equivalents to which such claims are entitled.

The invention claimed is:

1. A method for providing aroma therapy to a pet, the method comprising:

installing a porous element in a housing, the housing defining a plurality of through holes and a cavity, the plurality of through holes extend from an exterior surface of the housing to the cavity, the porous element including a first substance;

impregnating the porous element with a second substance, the second substance being a bodily fluid from an owner of the pet; and attaching the housing to a pet, wherein while attached to the pet, the first substance evaporates from the porous element and is inhaled by the pet.

2. The method of claim 1, wherein the first substance is a medication.

3. The method of claim 1, wherein the porous element is impregnated with the second substance prior to installing the porous element in the housing.

4. The method of claim 1, wherein attaching the housing to the pet includes attaching the housing to a collar of the pet.

5. The method of claim 1, wherein attaching the housing to the pet includes attaching the housing to a bridal of the pet.

6. The method of claim 1, further comprising select a size of the porous element based on a dosage of the first substance to be administered to the pet.

7. The method of claim 1, further comprising installing a second porous element in the housing, the second porous element impregnated with a second substance.

8. The method of claim 7,
wherein installing the first porous element in the housing includes installing the first porous element at a first end of the housing, and
wherein installing the second porous element in the housing includes installing the second porous element at a second end of the housing.

9. The method of claim 1, further comprising diluting the first substance with a dilution substance.

10. The method of claim 9, further comprising flashing off the dilution substance.

11. The method of claim 9, wherein the dilution substance does not form an azeotrope with the first substance.

12. The method of claim 9, wherein the first substance has a first vaporization temperature and the dilution substance has a dilution vaporization temperature, the dilution vaporization temperature being less than the first vaporization temperature.

13. The method of claim 1, further comprising swabbing the second substance from skin of the owner of the pet.

14. The method of claim 1, wherein the first substance is a perfume.

15. The method of claim 1, wherein the first substance is a bodily fluid from a parent of the pet.

16. The method of claim 1, wherein the first substance is a bodily fluid from a sibling of the pet.

17. The method of claim 1, wherein the first substance is sweat from a parent of the pet.

18. The method of claim 1, wherein the first substance is sweat from a sibling of the pet.

19. The method of claim 1, wherein the first element is a plant oil.

20. The method of claim 1, wherein the first element is an essential oil.

\* \* \* \* \*